(12) United States Patent
Van Dorpe et al.

(10) Patent No.: US 11,096,608 B2
(45) Date of Patent: Aug. 24, 2021

(54) DEVICE AND METHOD FOR NON-INVASIVE MEASURING OF ANALYTES

(71) Applicant: IMEC VZW, Leuven (BE)

(72) Inventors: Pol Van Dorpe, Spalbeek (BE); Peter Peumans, Herfelingen (BE)

(73) Assignee: IMEC vzw, Leuven (BE)

( * ) Notice: Subject to any disclaimer, the term of this patent is extended or adjusted under 35 U.S.C. 154(b) by 277 days.

(21) Appl. No.: 15/100,067

(22) PCT Filed: Dec. 3, 2014

(86) PCT No.: PCT/EP2014/076457
§ 371 (c)(1),
(2) Date: May 27, 2016

(87) PCT Pub. No.: WO2015/082564
PCT Pub. Date: Jun. 11, 2015

(65) Prior Publication Data
US 2017/0100064 A1    Apr. 13, 2017

(30) Foreign Application Priority Data

Dec. 3, 2013 (EP) .................................... 13195469

(51) Int. Cl.
*A61B 5/00* (2006.01)
*A61B 5/1455* (2006.01)
(Continued)

(52) U.S. Cl.
CPC .......... *A61B 5/1455* (2013.01); *A61B 5/0066* (2013.01); *A61B 5/0075* (2013.01);
(Continued)

(58) Field of Classification Search
CPC ............... G01N 2201/0636; G01N 2201/0633
See application file for complete search history.

(56) References Cited

U.S. PATENT DOCUMENTS

| 6,144,869 A | * | 11/2000 | Berner | ............... A61B 5/14532 600/309 |
| 6,219,575 B1 | * | 4/2001 | Nemati | ................ A61B 5/0059 128/898 |

(Continued)

OTHER PUBLICATIONS

PCT International Search Report and Written Opinion, PCT International Application No. PCT/EP2014/076457, dated Feb. 18, 2015.
(Continued)

*Primary Examiner* — Christian Jang
(74) *Attorney, Agent, or Firm* — McDonnell Boehnen Hulbert & Berghoff LLP (57) ABSTRACT

The present disclosure relates to devices and methods for non-invasive measuring of analytes. At least one embodiment relates to a wearable system for non-invasive measuring of a concentration of an analyte in skin tissue. The wearable system includes an integrated circuit that includes a first optical unit. The first optical unit includes a Raman spectrometer. The first optical unit also includes an OCT spectrometer and an interferometer optically coupled to the OCT spectrometer or an infrared (IR) spectrometer. The first optical unit additionally includes a light coupler. The wearable system further includes a first light source for performing Raman spectroscopy. The wearable system additionally includes a second light source for performing OCT spectroscopy or IR spectroscopy. Still further, the wearable system includes read-out electronics to determine an optical model of the skin tissue based on the spectroscopic data and to determine the concentration of the analyte.

19 Claims, 6 Drawing Sheets

(51) Int. Cl.
- *A61B 5/145* (2006.01)
- *G01N 21/65* (2006.01)
- *G01J 3/02* (2006.01)
- *G01J 3/44* (2006.01)
- *G01B 9/02* (2006.01)
- *G01N 21/35* (2014.01)

(52) U.S. Cl.
CPC ........ *A61B 5/1451* (2013.01); *A61B 5/14532* (2013.01); *A61B 5/443* (2013.01); *A61B 5/681* (2013.01); *G01J 3/0256* (2013.01); *G01J 3/0291* (2013.01); *G01J 3/44* (2013.01); *G01N 21/65* (2013.01); *A61B 2562/0233* (2013.01); *G01B 9/02091* (2013.01); *G01N 21/35* (2013.01); *G01N 2201/0633* (2013.01); *G01N 2201/0636* (2013.01); *G01N 2201/12* (2013.01)

(56) References Cited

U.S. PATENT DOCUMENTS

| | | | | |
|---|---|---|---|---|
| 6,725,073 | B1* | 4/2004 | Motamedi | A61B 5/0066 600/316 |
| 6,892,002 | B2* | 5/2005 | Christoffersen | G02B 5/1852 359/558 |
| 7,020,508 | B2* | 3/2006 | Stivoric | A61B 5/0205 600/390 |
| 2001/0055462 | A1* | 12/2001 | Seibel | A61B 1/00048 385/147 |
| 2006/0276696 | A1* | 12/2006 | Schurman | A61B 5/0066 600/316 |
| 2009/0021724 | A1* | 1/2009 | Mahadevan-Jansen | A61B 5/0066 356/73 |
| 2009/0073439 | A1* | 3/2009 | Tearney | A61B 5/0075 356/337 |
| 2009/0156905 | A1* | 6/2009 | Ries | A61B 5/0084 600/300 |
| 2011/0112591 | A1* | 5/2011 | Seymour | A61B 5/04001 607/3 |
| 2011/0313299 | A1* | 12/2011 | Brennan, III | A61B 5/0086 600/478 |
| 2012/0035442 | A1* | 2/2012 | Barman | A61B 5/14532 600/316 |
| 2012/0129269 | A1* | 5/2012 | Choi | G01J 3/02 436/164 |
| 2012/0226118 | A1* | 9/2012 | Delbeke | A61B 5/0031 600/316 |
| 2013/0060105 | A1* | 3/2013 | Shah | A61B 5/742 600/316 |

OTHER PUBLICATIONS

Larin, Kirill V. et al., "Monitoring Refractive Index Variations in Turbid Media Using Phase-Sensitive Frequency-Domain OCT", Proceedings of SPIE, vol. 5690, Apr. 13, 2005, pp. 422-425.

Robles, Francisco et al., "Assessing Hemoglobin Concentration Using Spectroscopic Optical Coherence Tomography for Feasibility of Tissue Diagnostics", Biomedical Optics Express, vol. 1, No. 1, Aug. 2, 2010, pp. 310-317.

"Optical coherence tomography and Raman spectroscopy of the ex-vivo retina"; authors: Julia W. Evans, et al.; published in: J Biophotonics. Jul. 2009 ; 2(6-7): 398-406. doi:10.1002/jbio. 200910022.

* cited by examiner

DEVICE AND METHOD FOR NON-INVASIVE MEASURING OF ANALYTES

CROSS-REFERENCE TO RELATED APPLICATION

The present application is a national stage entry of PCT/EP2014/076457 filed Dec. 3, 2014, which claims priority to European Patent Application No. 13195469.5 filed on Dec. 3, 2013, the contents of each of which are hereby incorporated by reference.

FIELD OF THE INVENTION

The disclosure relates to techniques for non-invasive measuring of analytes. In particular, the disclosure relates to techniques for non-invasive measuring of analytes in skin tissue using Raman spectroscopy and at least one of optical coherence tomography measurements and infrared measurements.

BACKGROUND OF THE INVENTION

Raman spectroscopy is a known technique for identifying molecules. The identification is based on vibrational information specific to chemical bonds and symmetry of molecules. The technique provides a fingerprint by which molecules may be identified. Raman spectroscopy can also be used to identify molecules in the skin of an individual and to estimate the total number of such molecules in the volume probed by the Raman measurement. However, due to the differences in the local geometry of the skin (e.g. different thicknesses and microstructure of the various layers that make up skin) it is difficult to quantify the concentration of a particular analyte without performing calibration steps for each individual separately. This is a time consuming and cumbersome process that limits the applicability of the Raman technique to do routine non-invasive measurements of important analytes such as glucose, cholesterol, ethanol, etc.

State of the art document "Optical coherence tomography and Raman spectroscopy of the ex-vivo retina", published in: "J Biophotonics. 2009 July; 2 (6-7): 398-406. doi: 10.1002/jbio.200910022" describes an OCT microscope for ex-vivo imaging combined with Raman spectroscopy to collect morphological and molecular information from a sample. A first disadvantage of the described device is the size of the device which makes it unsuitable for use in wearable applications. A second disadvantage is the high cost of the device due to the use of microscopes. As a third disadvantage, the device cannot be used to perform measurements at multiple locations of a sample at the same time. This makes the device less suitable for performing measurements on living tissue.

There is a need for cheap, compact and sensitive Raman based devices for determining the concentration of analytes in tissue without any of the drawbacks described above.

SUMMARY OF THE INVENTION

It is an object of the present invention to provide a user friendly sensor and method for determining a concentration of an analyte in a living object, e.g. for determining a glucose concentration in a human body. It is an advantage of embodiments of the present invention that a sensor and method for accurately determining a concentration of an analyte in a living object and this in a reliable and reproducible manner. It thereby is an advantage that a double sensing technique is used, allowing to take into account local variations in the skin tissue.

It is an advantage of embodiments of the present invention to provide a cheap and compact sensing device for determining the concentration of an analyte in tissue. It is an advantage of embodiments of the present invention to provide a non-invasive technique for determining the concentration of an analyte in tissue. It is an advantage of embodiments of the present invention to provide a device and technique for determining the concentration of an analyte in complex living tissue such as multilayer tissues, e.g. skin tissue. It is an advantage of the present invention to supply a device which can determine the concentration of an analyte in tissue in fast manner.

It is an advantage of embodiments of the present invention that fast measurements of an analyte in a living body can be obtained in a reproducible manner, using a wearable sensor system.

In a first aspect, the present invention relates to a wearable system for non-invasive measuring of the concentration of an analyte in skin tissue, the system comprising:

an integrated circuit comprising an integrated first optical unit comprising a RAMAN spectrometer, an OCT spectrometer and an interferometer optically coupled to the OCT spectrometer and/or an infrared spectrometer, a light coupler, positioned to couple scattered and/or reflected light from illuminated skin tissue into the RAMAN spectrometer and into the OCT spectrometer and/or the infrared spectrometer, a first light source optically coupled to or integrated in the integrated circuit and configured to emit a laser beam for performing Raman spectroscopy, a second light source optically coupled to or integrated in the integrated circuit and configured to emit a broadband light beam for performing OCT spectroscopy or IR spectroscopy, and read-out electronics electrically coupled to the integrated circuit and configured for reading out spectroscopic data from the RAMAN spectroscopy, for reading out spectroscopic data from the OCT spectrometer and/or the IR spectrometer, for determining an optical model of the skin tissue based on the spectroscopic data from the OCT spectrometer and/or the IR spectrometer, and for determining the concentration of an analyte based on a correlation between the spectroscopic data from the RAMAN spectroscopy and the determined optical model of the skin tissue.

The read-out electronics may be configured for determining the optical model of the skin tissue comprising thicknesses and optical properties of different layers of the skin tissue.

The read-out electronics may be configured for determining the skin tissue model comprising information on the refractive index of interstitial fluid and blood in the tissue.

The read-out electronics may be configured for reading out the RAMAN spectroscopic data substantially simultaneously with the OCT and/or IR spectroscopic data and for determining the physical model based on said OCT and/or IR spectroscopic data.

The system may be completely packaged in a wearable casing and wherein the wearable casing is adapted to press the integrated circuit against the skin tissue of an individual when worn thereby allowing scattered and reflected light from illuminated skin tissue to be received by the integrated circuit.

The wearable casing may be a wristband, the size of the wristband being adaptable to allow pressing of the integrated circuit against the skin of an individual when worn.

The wearable casing may be a watch comprising a watch strap, the size of the watch strap being adaptable to allow pressing of the integrated circuit against the skin of an individual when worn.

The wearable system may comprise both an IR spectrometer and an OCT spectrometer, the wearable system further comprising a third light source optically coupled to the integrated circuit and configured to emit a broadband light beam, so that the second light source and the third light source each provide a broadband light beam to one of the IR spectroscopy or OCT spectroscopy; and wherein the readout electronics further may be configured to read out and correlate spectroscopic data from the RAMAN, OCT and IR spectrometer and determine the concentration of an analyte using the correlated spectroscopic data.

The second light source may be a low coherent light source or a very wide bandwidth source and wherein the third light source may be low coherent light source or a very wide bandwidth source.

The system further may comprise at least one optical reflector adapted to couple light from a light source in the integrated circuit.

The integrated circuit may comprise an imaging region optically coupled to the RAMAN spectrometer and to the OCT spectrometer and/or the infrared spectrometer.

The present invention also relates to a method for non-invasive measuring of the concentration of analyte in skin tissue using the wearable system as described above, the method comprising:

substantially simultaneously obtaining spectra of Raman scattered light and one or both of OCT spectra and IR spectra in a non-invasive way at the skin tissue;

obtaining an optical model of the skin tissue based on one or both of the obtained OCT spectra and IR spectra;

correlating the obtained spectroscopic Raman data with the obtained optical model;

and determining the concentration of the analyte using the correlated data.

Obtaining an optical model may comprise obtaining an optical model of the skin tissue comprising thicknesses and optical properties of different layers of the tissue.

Obtaining an optical model may comprise obtaining an optical tissue model comprising information on the refractive index of interstitial fluid and blood in the tissue.

Substantially simultaneously obtaining may comprise substantially simultaneously obtaining Raman spectroscopic data, OCT spectroscopic data and IR spectroscopic data.

The method may comprise obtaining a skin model of skin tissue underneath the sensor, the skin model comprising information on thickness and optical properties of different layers of the skin tissue.

The skin model further may comprise information on the refractive index of interstitial fluid and blood in the skin tissue.

The analyte may be glucose.

Obtaining Raman spectra may comprise simultaneously obtaining spectra of Raman scattered light of the tissue at different locations.

The present invention also relates to the use of the system as described above for measuring the concentration of glucose in living tissue. In a further aspect of the present invention, an integrated circuit for performing spectroscopy on tissue is presented. The device comprises: a first optical unit comprising: a RAMAN spectrometer; an OCT spectrometer; an interferometer optically coupled to the OCT spectrometer; and a light coupler, positioned to couple scattered and reflected light from illuminated tissue into the RAMAN and OCT spectrometer; and an imaging region optically coupled to the RAMAN and OCT spectrometer.

According to an embodiment of the present invention the integrated circuit further comprises at least a second optical unit, wherein the imaging region is optically coupled to the RAMAN and OCT spectrometer of each optical unit.

According to an embodiment of the present invention, the first optical unit further comprises an IR spectrometer optically coupled to the light coupler; and further comprising an infrared imaging region optically coupled to the IR spectrometer.

In a second aspect of the present invention, an integrated circuit for performing spectroscopy on tissue is presented. The device comprises: a first optical unit comprising: a RAMAN spectrometer; an IR spectrometer; a light coupler, positioned to couple scattered and reflected light from illuminated tissue into the RAMAN and IR spectrometer; an imaging region optically coupled to the RAMAN spectrometer; and an infrared imaging region optically coupled to the IR spectrometer.

According to an embodiment of the present invention, the integrated circuit further comprises at least a second optical unit; wherein the imaging region is optically coupled to the RAMAN spectrometer of each optical unit; and wherein the infrared imaging region is optically coupled to the IR spectrometer of each optical unit.

According to an embodiment of the present invention, the first optical unit further comprises: an OCT spectrometer optically coupled to light coupler; and an interferometer optically coupled to the OCT spectrometer; and wherein the imaging region is optically coupled to the OCT spectrometer.

According to an embodiment of the present invention, the integrated circuit further comprises at least a second optical unit; wherein the imaging region is optically coupled to the RAMAN and OCT spectrometer of each optical unit; and wherein the infrared imaging region is optically coupled to the IR spectrometer of each optical unit.

According to an embodiment of the present invention, the integrated circuit further comprises at least one optical waveguide distributor for distributing a light beam of a light source on the integrated circuit thereby allowing simultaneous illumination of one or different locations of tissue.

According to an embodiment of the disclosure, the integrated circuit further comprises at least one through-hole thereby allowing illumination of tissue through the integrated circuit.

According to an embodiment of the present invention, the integrated circuit further comprises at least one rejection filter located to allow, when in operation, only scattered light reaching the RAMAN spectrometer.

According to an embodiment of the present invention, the integrated circuit comprises a plurality of active electronic component layers thereby forming a three-dimensional integrated circuit wherein each active electronic component layer comprises the first optical unit or the at least one second optical unit. The integrated circuit may be a 3D (stacked) integrated circuit comprising different layers, each layer comprising an optical unit.

According to an embodiment of the present invention, the light coupler of the first or the at least one second optical unit of each active electronic component layer is configured to couple light with a different wavelength into the RAMAN spectrometer. Each light coupler of an optical unit present in a layer of the 3D integrated circuit may be configured to couple light with a specific wavelength in a spectrometer. The wavelength ranges of different light couplers may be adjacent to allow in coupling of light with wavelengths falling within a specific wavelength range.

According to an embodiment of the present invention, one or more photodiodes of the imaging region comprise a spectral filter for spectrally resolving RAMAN scattered light. At least one photodiode in the imaging region, which may be present in an active electronic component layer of the integrated circuit, may comprise a spectral filter. Different photodiodes of the imaging region may comprise different spectral filters.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS OF THE PRESENT INVENTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Throughout the description of the different embodiments reference may be made to a "silicon substrate". It should be understood that these embodiments apply equally well to other substrates. In embodiments, the term "silicon substrate" may include a substrate such as e.g. a silica (SiO2) substrate, a silicon germanium (SiGe) substrate or a glass silicon substrate. It may also refer to the ensemble of one or more layers present on that substrate, e.g. an isolating layer on a silicon substrate wherein the silicon substrate comprises an isolating layer and a silicon substrate. The term "silicon substrate" also includes silicon-on-glass, silicon-on-sapphire silicon substrates.

Throughout the description reference may be made to "reflected light". This may refer to "backscattered light" in which backscattering is the reflection of waves, particles, or signals back to the direction from which they came. It may be a diffuse reflection.

The method and device presented in embodiments of the present invention offer a solution for the detection or measurement of the concentration of an analyte in complex living tissue. Such tissue may comprise multiple layers wherein each layer may have a different structure at one or different locations of the tissue, e.g. textile, skin tissue. When such tissue is illuminated, scattered light spreads out across different angles based on the different layers and the different structure of the tissue. This poses a problem when identifying an analyte based on the scattered light.

The method and device presented in embodiments of the present invention characterizes the structure of living tissue and uses this information to calibrate Raman measurements in real-time. Thus, Raman spectroscopy is combined with at least one other optical spectroscopy technique to determine the concentration of an analyte in a tissue.

In a first aspect of the disclosure, an integrated circuit 100 for determining the concentration of an analyte in tissue is presented. The integrated circuit 100 comprises: a first optical unit comprising: a RAMAN spectrometer (102); an OCT spectrometer (103); an interferometer (104) optically coupled to the OCT spectrometer; and a light coupler (105), positioned to couple scattered and reflected light from illuminated tissue into the RAMAN and OCT spectrometer (102, 103); and an imaging region (106) optically coupled to the RAMAN and OCT spectrometer (102, 103). This configuration is illustrated in a block diagram in FIG. 1. The integrated circuit may be monolithically integrated wherein optical components are monolithically integrated with on-chip electronics. The co-integration of optics and electronics on the same chip allows high functionality, high performance and renders a highly integrated device which is compact and portable. This allows the device to be used in wearable applications.

According to an embodiment of the disclosure, the integrated circuit is a CMOS chip.

Figure 1:
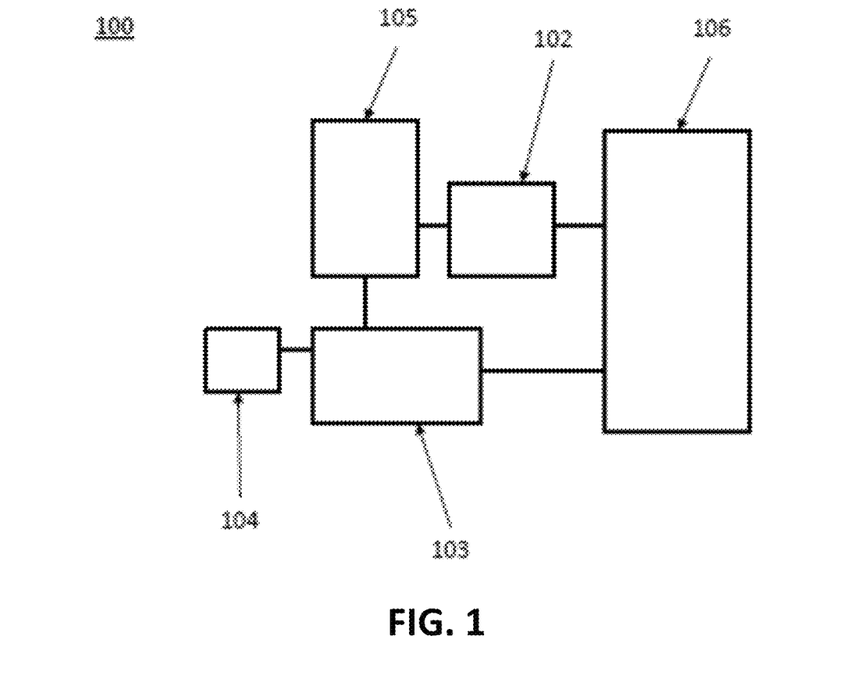
FIG. 1 illustrates a block diagram of an integrated circuit configured to perform RAMAN and OCT spectroscopy, as can be used in an embodiment of an aspect of the present invention.

The integrated circuit presented in the first aspect of the disclosure may be configured to simultaneously perform Raman spectroscopy and OCT spectroscopy. Spectral data from both techniques may be combined to determine the concentration of an analyte in tissue. Both spectroscopy techniques can be combined on a single chip, e.g. a CMOS chip. The first optical unit comprises a Raman spectrometer, an OCT spectrometer, an interferometer and a light coupler. The RAMAN spectrometer may be an on-chip spectrometer for spectrally resolving an incoming optical signal. The RAMAN spectrometer may be an on-chip Arrayed Waveguide Grating (AWG) spectrometer, a grating or a planar concave grating. The OCT spectrometer may be an on-chip OCT spectrometer. The interferometer is optically coupled to the OCT spectrometer. The interferometer is adapted to receive a reference light beam. The light coupler is positioned such that scattered and reflected light from illuminated tissue can reach the light coupler. The light coupler is optically coupled to the RAMAN and the OCT spectrometer. The light coupler couples RAMAN scattered light and reflected light from tissue respectively into the RAMAN and the OCT spectrometer. The light coupler may be a grating coupler. The optical coupling between the light coupler and the RAMAN and OCT spectrometer may be a plurality of optical waveguides. Further, the RAMAN and OCT spectrometer are optically coupled to the imaging region. The imaging region may be an image sensor wherein the sensitive side of the image sensor, e.g. the side comprising photodiodes, may be attached to a surface of the substrate of the integrated circuit. The imaging region senses spectrally resolved RAMAN scattered light and spectrally resolved reflected light from the tissue. The RAMAN spectrometer may be optically coupled via a plurality of waveguides to a grating coupler which couples spectrally resolved light from the RAMAN spectrometer in the imaging region. The OCT spectrometer may be optically coupled to another grating coupler via a plurality of waveguides, which couples spectrally resolved light from the OCT spectrometer in the imaging region. If the imaging region is an image sensor, the grating couplers may be positioned in between the substrate of the integrated circuit and the sensing side of the image sensor, allowing light from the grating coupler to be sensed by the image sensor.

According to an embodiment of the disclosure, the light coupler comprises a RAMAN light coupler. The RAMAN light coupler may be a tunable multilevel grating configured for broadband, broad-angular-range in coupling of RAMAN scattered photons.

According to an embodiment of the disclosure, the integrated circuit further comprises at least a second optical unit, wherein the imaging region 106 is optically coupled to the RAMAN and OCT spectrometer 102, 103 of each optical unit.

To perform Raman and OCT spectroscopy at one or different locations of tissue, the integrated circuit comprises multiple optical units. Each optical unit can simultaneously perform Raman and OCT spectroscopy. Different optical units can simultaneously perform Raman and OCT spectroscopy. It is an advantage of the disclosure that RAMAN and OCT spectroscopy may be performed in parallel. This allows the integrated circuit to function in snap-shot mode whereby different spectroscopic measurements can be done at the same time. This is important to cancel out volume changes of the tissue underneath the integrated circuit which may occur over time.

According to embodiments of the disclosure, the first optical unit further comprises an IR spectrometer (107) optically coupled to the light coupler (105); and further comprising an infrared imaging region (108) optically coupled to the IR spectrometer (107). This configuration is illustrated in a block diagram in FIG. 3.

Figure 3:
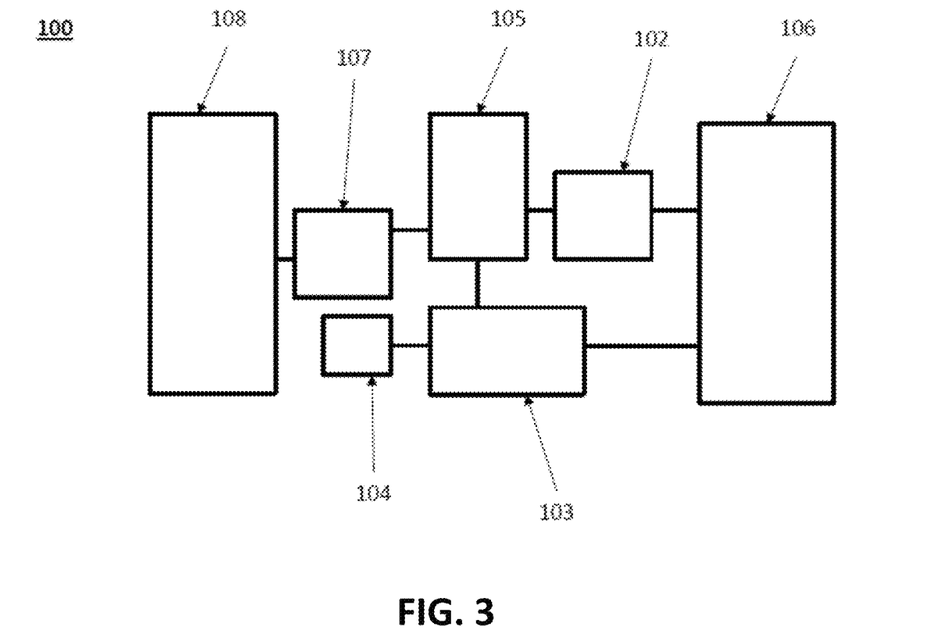
FIG. 3 illustrates a block diagram of an integrated circuit configured to perform RAMAN, OCT and IR spectroscopy, as can be used in an embodiment of an aspect of the present invention.

The integrated circuit may be configured to simultaneously perform Raman spectroscopy, OCT spectroscopy and IR spectroscopy. Spectral data from the three spectroscopic techniques may be used to determine the concentration of an analyte in tissue. As an advantage, the three spectroscopy techniques are combined on a single chip to improve the accuracy of the determination of an analyte in complex tissue such as e.g. skin tissue. The light coupler is optically connected to the IR spectrometer via a plurality of waveguides. The light coupler couples reflected infrared light from tissue into the IR spectrometer. Further, the IR spectrometer is optically connected to an infrared imaging region. If the infrared imaging region is an infrared image sensor, the sensitive side of the infrared image sensor, e.g. the side comprising photodiodes, may be attached to the integrated circuit. The infrared imaging region may be an Indium Gallium Arsenide (InGaAs) imaging region suitable for near infrared (NIR) and/or short wave infrared (SWIR) imaging. The infrared imaging region senses spectrally resolved reflected infrared light from the IR spectrometer. Spectrally resolved light from the IR spectrometer may be coupled into the infrared imaging region via a grating coupler which is optically connected to the IR spectrometer via a plurality of optical waveguides. If the infrared imaging region is an infrared image sensor, the grating coupler may be positioned in between the substrate of the integrated circuit and the sensing side of the infrared image sensor.

In a second aspect of the disclosure, an integrated circuit 100 is presented. This is illustrated in the block diagram of FIG. 2. The integrated circuit 100 comprises: a first optical unit comprising: a RAMAN spectrometer (102); an IR spectrometer (107); a light coupler (105), positioned to couple scattered and reflected light from illuminated tissue into the RAMAN and IR spectrometer (102, 107); an imaging region (106) optically coupled to the RAMAN spectrometer (102); and an infrared imaging region (108) optically coupled to the IR spectrometer (107).

Figure 2:
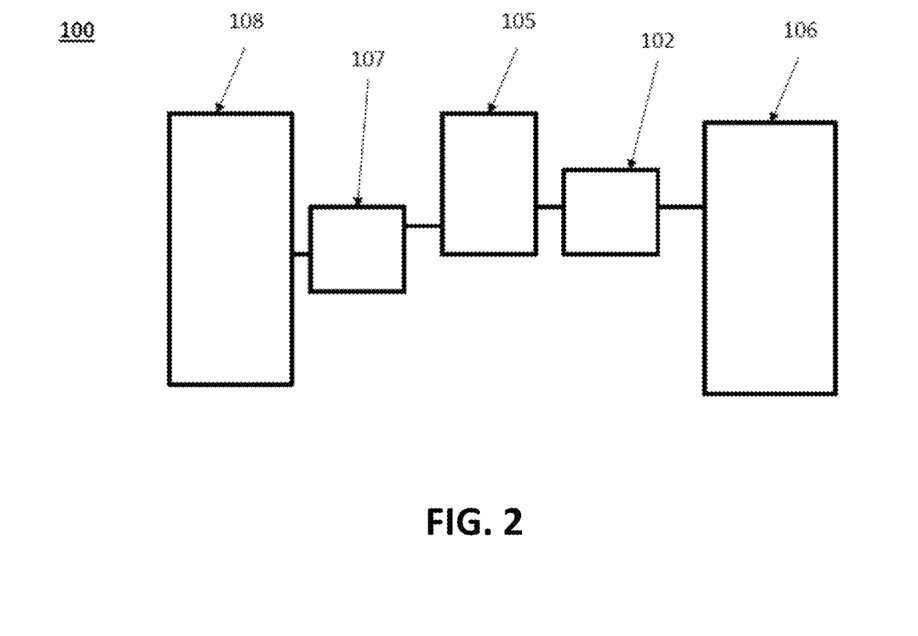
FIG. 2 illustrates a block diagram of an integrated circuit configured to perform RAMAN and IR spectroscopy, as can be used in an embodiment of an aspect of the present invention.

The integrated circuit presented in the second aspect of the disclosure may be configured to simultaneously perform Raman spectroscopy and IR spectroscopy and may combine IR and RAMAN spectroscopic data to determine the concentration of an analyte in tissue. The RAMAN spectrometer may be an on-chip spectrometer for spectrally resolving an incoming optical signal. For example, the RAMAN spectrometer may be an on-chip Arrayed Waveguide Grating (AWG) spectrometer, a grating or a planar concave grating. The light coupler is positioned to allow scattered and reflected infrared light from tissue to reach the light coupler. The light coupler is optically connected to the RAMAN and the IR spectrometer via a plurality of waveguides. The light coupler couples RAMAN scattered light and reflected infrared light into respectively the RAMAN and the IR spectrometer. The light coupler may be a grating coupler. Further, the RAMAN spectrometer is optically coupled to an imaging region. If the imaging region is an image sensor, the sensitive side, e.g. the side comprising photodiodes, may be attached to the substrate of the integrated circuit. The imaging region senses spectrally resolved RAMAN scattered light from tissue. Spectrally resolved light from the RAMAN spectrometer may be coupled into the imaging region via a grating coupler. The grating coupler may be connected to the RAMAN spectrometer via a plurality of optical waveguides. If the imaging region is an image sensor, the grating coupler may be positioned in between the substrate of the integrated circuit and the sensing side of the image sensor. The IR spectrometer is optically connected to an infrared imaging region. If the infrared imaging region is an infrared image sensor, the sensitive side, e.g. the side comprising photodiodes, may be attached to the substrate of the integrated circuit. The infrared imaging region senses spectrally resolved reflected infrared light from tissue. The spectrally resolved infrared light from the IR spectrometer may be coupled into the infrared imaging region using a grating coupler. The grating coupler may be connected to the IR spectrometer via a plurality of optical waveguides. If the infrared imaging region is an infrared image sensor, the grating coupler may be positioned in between the substrate of the integrated circuit and the sensing side of the infrared image sensor.

According to an embodiment of the disclosure, the integrated circuit further comprises at least a second optical unit; wherein the imaging region (106) is optically coupled to the RAMAN spectrometer of each optical unit; and wherein the infrared imaging region (108) is optically coupled to the IR spectrometer of each optical unit.

To perform Raman and IR spectroscopy at one or different locations of tissue, at the same time, the integrated circuit comprises multiple optical units. Each optical unit can simultaneously perform Raman and IR spectroscopy. Different optical units can simultaneously perform Raman and IR spectroscopy. It is an advantage of the disclosure that RAMAN and IR spectroscopy may be performed in parallel. This allows the integrated circuit to function in snap-shot mode whereby different spectroscopic measurements can be done at the same time.

According to an embodiment of the disclosure, the first optical unit further comprises: an OCT spectrometer (103) optically coupled to light coupler (105); and an interferometer (104) optically coupled to the OCT spectrometer (103); and wherein the imaging region (106) is optically coupled to the OCT spectrometer (103). This configuration is illustrated in block diagram FIG. 3.

The integrated circuit may be configured to perform Raman spectroscopy, OCT spectroscopy and IR spectroscopy. As an advantage, three spectroscopic techniques may be combined on a single chip to improve the determination of the concentration of an analyte in complex tissue such as e.g. skin tissue.

The first optical unit may further comprise an OCT spectrometer and an interferometer. The interferometer may be adapted for receiving a reference light beam. The light coupler is optically connected to the OCT spectrometer. The light coupler couples reflected light from tissue into the OCT spectrometer. The optical connection between the light coupler and the OCT spectrometer may be a plurality of optical waveguides. Further, the OCT spectrometer is optically connected to the imaging region of the integrated circuit. The imaging region senses spectrally resolved reflected light from the OCT spectrometer. A plurality of optical waveguides optically interconnects the OCT spectrometer with a grating coupler which couples the spectrally resolved reflected light from the OCT spectrometer into the imaging region sensor. If the imaging region is an image sensor, the grating coupler may be positioned in between the substrate of the integrated circuit and the sensing side of the image sensor.

According to an embodiment of the disclosure, the integrated circuit 100 further comprises at least a second optical unit; wherein the imaging region 106 is optically coupled to the RAMAN and OCT spectrometer of each optical unit; and wherein the infrared imaging region (108) is optically coupled to the IR spectrometer of each optical unit.

To simultaneously perform Raman, IR and OCT spectroscopy at one or different locations of tissue, the integrated circuit 100 comprises multiple optical units. Each optical unit can simultaneously perform Raman, IR and OCT spectroscopy. Different optical units can simultaneously perform Raman, IR and OCT spectroscopy. It is an advantage of the disclosure that RAMAN, IR and OCT spectroscopy may be performed in parallel. This allows the integrated circuit to function in snap-shot mode whereby different spectroscopic measurements can be done at the same time.

According to an embodiment of the disclosure, the integrated circuit 100 further comprises at least one optical waveguide distributor for distributing a light beam of a light source on the substrate thereby allowing simultaneous illumination of one or different locations of tissue.

The optical waveguide distributor may be an on-chip optical waveguide distribution device which comprises: an optical input and one or a plurality of optical outputs. In embodiments where illumination is performed on a plurality of locations, via a plurality of optical waveguides, the plurality of optical outputs may be located at different locations on the integrated circuit. A light source, e.g. a laser, may be optically coupled to the optical input. As an advantage, only a single light source is needed to illuminate different locations of tissue underneath the integrated circuit. As a further advantage, the cost of the integrated circuit may be reduced. The optical waveguide distributor may be fabricated from SiNx. As an advantage, low loss distribution of light on the integrated circuit can be achieved.

According to embodiments of the disclosure, the integrated circuit 100 comprises at least one through-hole 109 thereby allowing illumination of tissue through the integrated circuit 100.

The integrated circuit as presented in the first and second aspect of the disclosure or as presented in any of its embodiments may comprise at least one through-hole. Dimensions of the at least one through-hole may be adapted to allow a light beam to pass through the integrated circuit without any hindering. The at least one through-hole provides an improved excitation light path and optionally an improved optical scattered light collection. According to embodiments of the disclosure, the at least one through-hole may comprise a lens for focusing the light source. According to embodiments of the disclosure, the at least one through-hole may comprise an opaque ring for suppressing stray light.

According to embodiments of the disclosure, the integrated circuit 100 further comprises at least one rejection filter (110) located to allow, when in operation, only scattered light reaching the RAMAN spectrometer (102).

The at least one reflection filter is located and configured to reject or attenuate laser source frequency light and to allow a very sensitive measurement of the RAMAN scattered light. The at least one reflection filter may be a semiconductor structure configured to reject a strong excitation light signal, e.g. a laser at 785 nm. When combining Raman and OCT spectroscopy, a wavelength separation of reflected light and Raman scattered light may be done. The wavelength of the rejection filter may be configured based on the configuration of the integrated circuit. For example, when the integrated circuit is configured to perform Raman and OCT spectroscopy simultaneously, the different wavelength zones may be shifted. For example, if the OCT has a shorter wavelength than the rejection wavelength of the rejection filter. The rejection filter may be positioned to filter reflected light for performing OCT and Raman scattered light before reaching the light coupler.

According to an embodiment of the disclosure, the integrated circuit 100 may further comprise an optical window 110 which may be pressed against tissue, e.g. against skin tissue. The optical window 110 may be located on top of the light coupler 105 and may function as a protector for the light coupler 105. The optical window 110 may be fabricated from a transparent material, e.g. glass or a transparent polymer.

According to embodiments of the disclosure, optical waveguides that optically couple the light coupler, RAMAN, OCT and IR spectrometers, grating couplers and image sensors on the integrated circuit may be low loss Silicon Nitride (SiNx) waveguides for visible, near infrared (NIR) and/or short wave infrared (SWIR) light. According to an embodiment of the disclosure, grating couplers used to couple light from a spectrometer into an image sensor may be SiNx out-coupling gratings. The material SiNx shows a low loss at visible and near-infrared wavelengths. As an advantage, the integrated circuit 100 is a highly sensitive device. As another advantage, the material SiNx may be used in Raman and OCT spectroscopy applications as the wavelength of light in both applications is situated in the visible range. Further, SiNx can easily be combined with standard CMOS optical detection technologies. For example, SiNx based photonics can be processed directly on top of CMOS imagers which can be used as a detector for visible wavelengths. This may be done in a post-processing step wherein SiNx optical components are processed on top of CMOS wafers containing e.g. CMOS imagers. As an advantage, the integrated circuit can be processed in a very compact way. It is a further advantage that SiNx components may be processed on top of commercially available image sensors thereby allowing SiNx components to be processed on top of integrated detectors. As an advantage, of-the-shelf components may be used thereby decreasing the cost of the integrated circuit.

Figure 4:
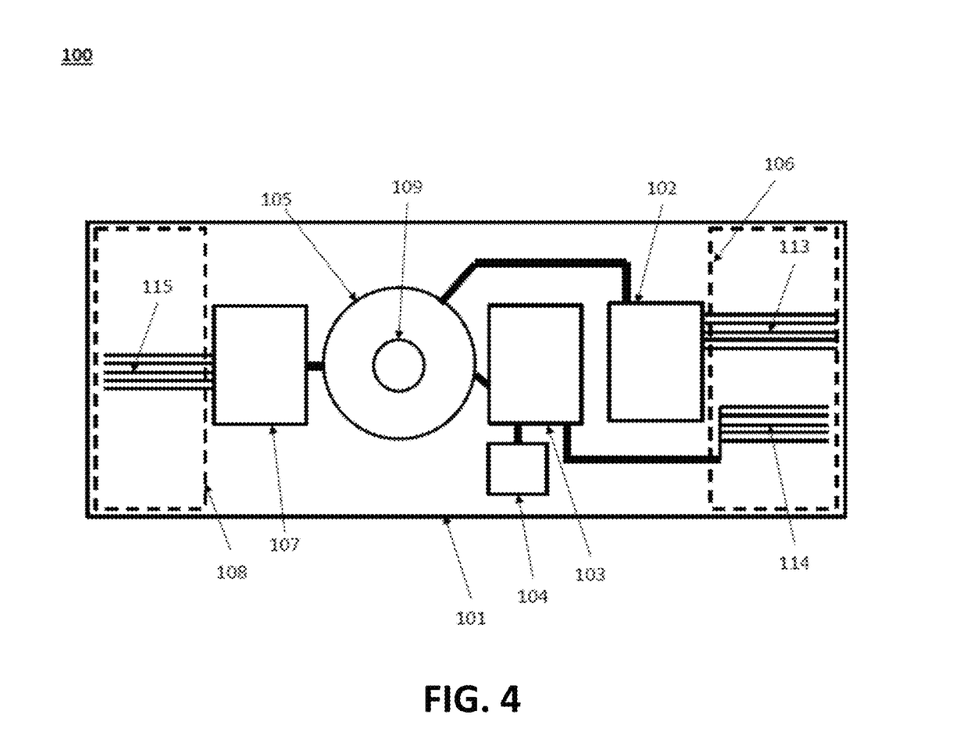
FIG. 4 illustrates a surface of an integrated circuit configured to perform RAMAN, OCT and IR spectroscopy according to an embodiment of the present invention.

FIG. 4 illustrates a bottom view of an embodiment of the first or second aspect of the disclosure. The integrated circuit 100 comprises: a silicon substrate, a through-hole 109; a light coupler 105 optically coupled to a RAMAN, an OCT and an IR spectrometer 102, 103, 107 and an interferometer 104. The RAMAN and OCT spectrometers are optically coupled to an imaging region 106 via different grating couplers 113, 114. An IR spectrometer 107 is optically coupled to an infrared imaging region 108 using a grating coupler 115. The interferometer 104 is optically coupled to the OCT spectrometer 103.

Figure 5:
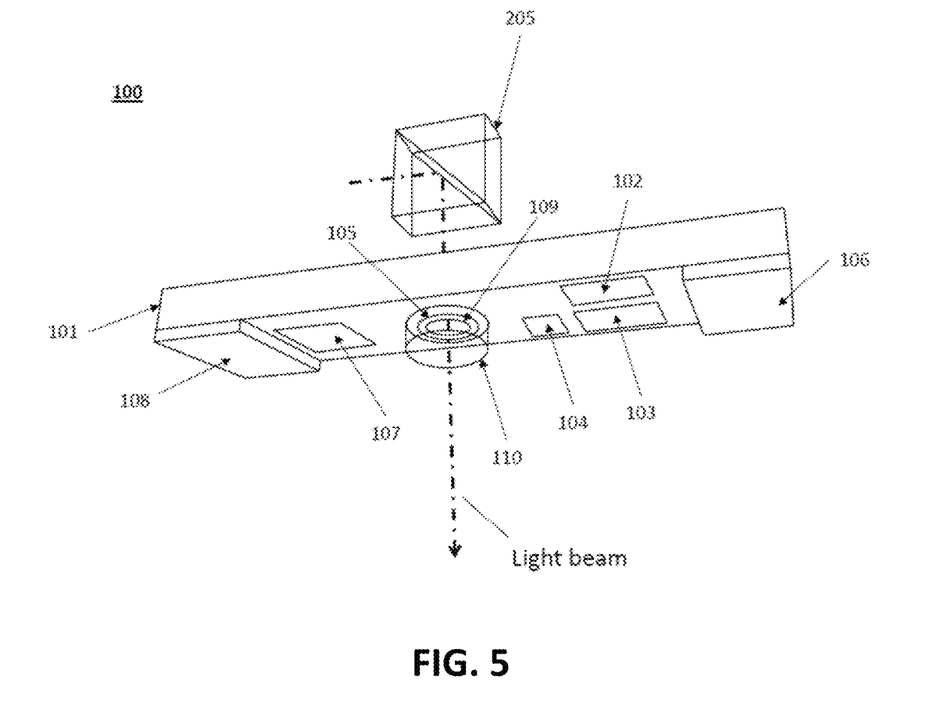
FIG. 5 is a 3D illustration of an integrated circuit configured to perform RAMAN, OCT and IR spectroscopy, an optical reflector and a light beam according to an embodiment of the disclosure

FIG. 5 illustrates an embodiment of the first or second aspect of the disclosure. The integrated circuit 100 comprises a silicon substrate 101. A surface of the substrate 101 comprises: a RAMAN, an OCT and an IR spectrometer 102, 103, 107 for spectrally resolving an optical signal; an interferometer 104 optically coupled to the OCT spectrometer 103; a first and a second image sensor 106, 108; a light coupler 105 for coupling light in the RAMAN, OCT and IR spectrometer 102, 103, 107; an optical window 110 covering the light coupler 105. Further, the substrate 101 comprises a through-hole 109 allowing a light beam to be directed through the integrated circuit 100.

Figure 6A:
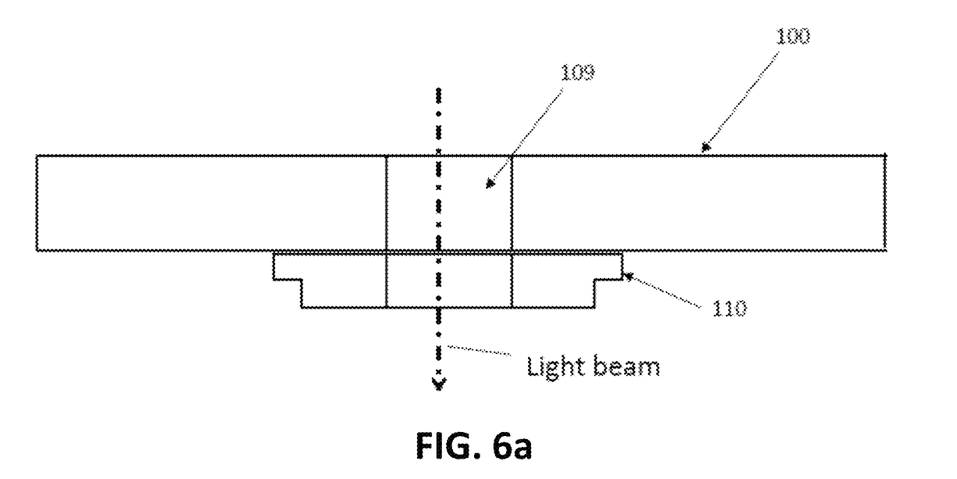
FIG. 6a illustrates a cross-section of an integrated circuit with an optical window attached to a surface according to an embodiment of the present invention.
Figure 6B:
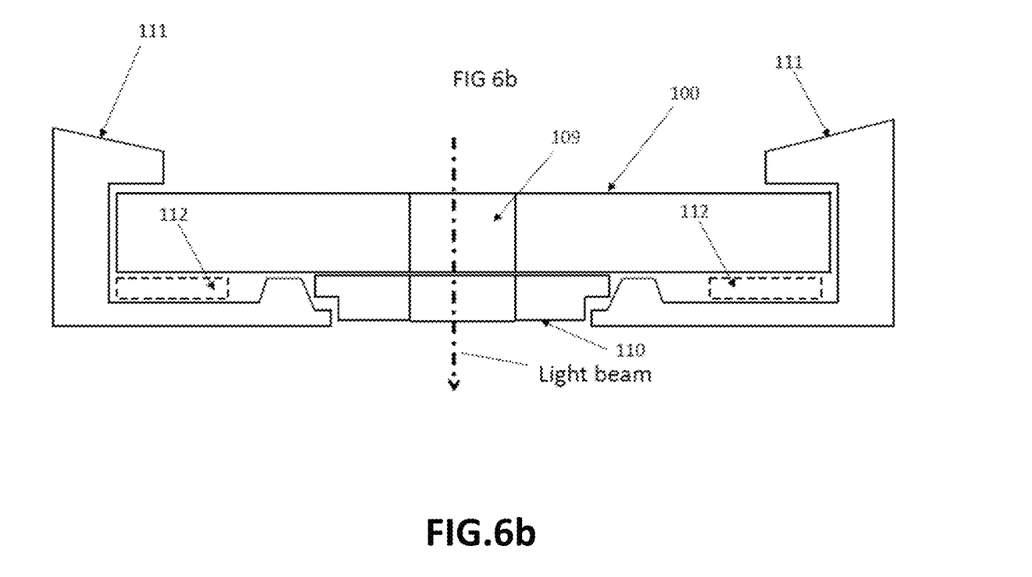
FIG. 6b illustrates a cross section of an integrated circuit in a casing according to an embodiment of the present invention.

FIG. 6a illustrates a cross-section of the integrated circuit 100. An optical window 110 is attached to a surface of the integrated circuit 100. FIG. 6b illustrates a cross-section of the integrated circuit 100 and a casing 111 for holding the integrated circuit 100. The casing 111 further comprises additional elements for holding the integrated circuit 100 firmly in the casing 111. These elements may be cushion elements 112 placed in between the integrated circuit 100 and the casing 111.

According to embodiments of the disclosure, the integrated circuit is a three-dimensional integrated circuit comprising a plurality of active electronic component layers wherein each layer comprises at least one optical unit. In this configuration, the different optical units are stacked vertically, on top of each other. As an advantage, the compactness of the integrated circuit is increased. The stacking of different optical units on top of each other also allows light with different wavelengths to be received by different optical units.

The light coupler of each stacked optical unit may be configured to couple RAMAN scattered light with a different wavelength into a RAMAN spectrometer. As an advantage, the integrated circuit may be configured to receive and spectrally resolve light with different wavelengths.

EXAMPLE

When the integrated circuit comprises three active electric component layers, each layer comprising an optical unit, the light coupler of the first layer may be configured to couple light with a wavelength of 820-850 nm into the RAMAN spectrometer of the optical unit of the first layer. The light coupler of the second layer may be configured to couple light with a wavelength of 850-880 nm into the RAMAN spectrometer of the optical unit of the second layer. The light coupler of the third layer may be configured to couple light with a wavelength of 880-910 nm into the RAMAN spectrometer of the optical unit of the third layer. In this configuration, the integrated circuit is capable of receiving and spectrally resolving RAMAN scattered light with a wavelength of 820-910 nm. In this example, the wavelength ranges of different light couplers are adjacent to extend the wavelength range of the integrated circuit.

To separate different active electronic component layers from each other, an isolating layer, e.g. an oxide layer, may be present in between different layers. The isolating layer may be a few micrometers thick, e.g. 1-2 micrometer.

According to embodiments of the disclosure, if the integrated circuit is a three dimensional integrated circuit, photodiodes of the imaging region and/or infrared imaging region may be located on different active electronic component layers of the three dimensional integrated circuit. Thus, photodiodes of an imaging region or an infrared imaging region are distributed across different layers. Spectrometers of an optical unit may be optically connected to photodiodes located in the layer comprising the optical unit.

According to embodiments of the disclosure, photodiodes of the imaging region may comprise spectral filters wherein a spectral filter is located on top of one or more photodiodes. Hence, light falling onto the photodiodes is filtered by at least one spectral filter before it is sensed by the imaging region. The wavelength range of spectral filters may be configured to resolve a spectrum of Raman scattered light. For example, the spectral filters may be configured to resolve the spectrum of an analyte, e.g. a bio-analyte, e.g. glucose. The spectral filters may be configured to have a resolution of a few nanometers, e.g. 1-2 nanometers. Hence, the spectral filters may be used to differentiate different peaks of a Raman spectrum. This may increase the speed of the identification of an analyte.

Figure 7:
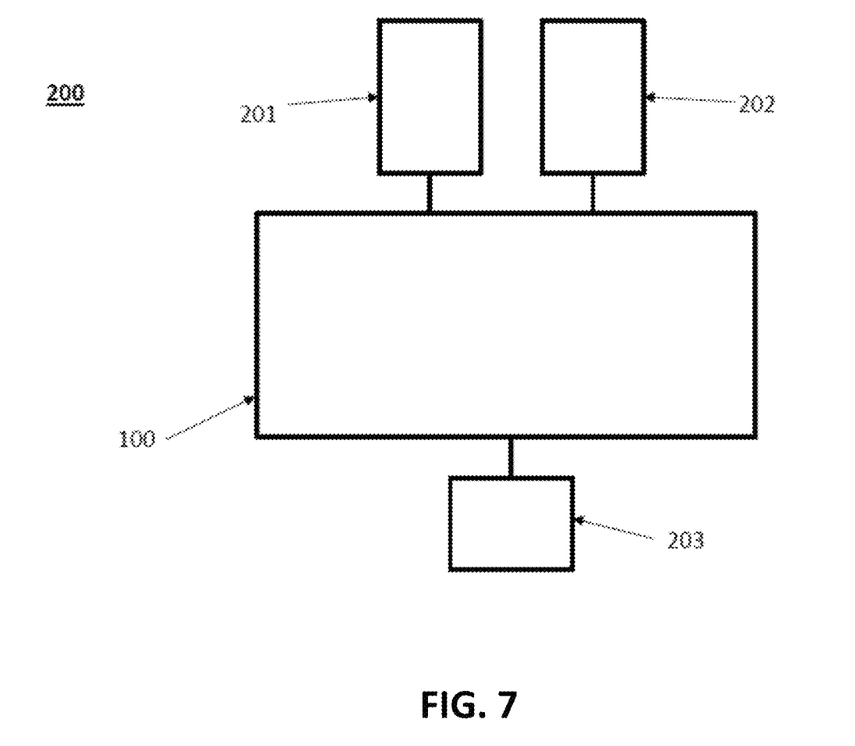
FIG. 7 illustrates a block diagram of a sensing system comprising an integrated circuit for performing RAMAN+OCT or RAMAN+IR spectroscopy, according to an embodiment of the present invention.

In a third aspect of the disclosure, a wearable system 200 for determining the concentration of an analyte in tissue in a non-invasive manner is presented. The system 200 comprises an integrated circuit comprising an integrated first optical unit comprising a RAMAN spectrometer, an OCT spectrometer and an interferometer optically coupled to the OCT spectrometer and/or an infrared spectrometer. The integrated circuit also comprises a light coupler, positioned to couple scattered and/or reflected light from illuminated skin tissue into the RAMAN spectrometer and into the OCT spectrometer and/or the infrared spectrometer. The integrated circuit (100) may be according to an embodiment of the first and second aspect of the present invention. The wearable system also comprises a first light source (201) optically coupled to or integrated in the integrated circuit (100) and configured to emit a laser beam for performing Raman spectroscopy; a second light source (202) optically coupled to or integrated in the integrated circuit (100) and configured to emit a broadband light beam for performing OCT spectroscopy or IR spectroscopy. The system also comprises read-out electronics (203) electrically coupled to the integrated circuit (100) and configured for reading out spectroscopic data from the RAMAN spectroscopy, for reading out spectroscopic data from the OCT spectrometer and/or the IR spectrometer, for determining an optical model of the kin tissue based on the spectroscopic data from the OCT spectrometer and/or the IR spectrometer and for determining the concentration of an analyte based on a correlation between the spectroscopic data from the RAMAN spectroscopy and the determined optical model of the skin tissue. An exemplary configuration is illustrated in FIG. 7.

The system as presented in the third aspect of the present invention can be used to determine the concentration of an analyte in a tissue in a non-invasive manner by combining: a) RAMAN spectroscopy and OCT spectroscopy or b) RAMAN spectroscopy and IR spectroscopy or even a combination of RAMAN spectroscopy with OCT spectroscopy and IR spectroscopy. The system 200 thus may comprise an integrated circuit as presented in an embodiment of the first or second aspect of the present invention. Further, it may comprise different light sources for illuminating tissue and read-out electronics for processing/correlating data from different spectrometers.

Determining the concentration of an analyte in tissue is performed by:
1) positioning the integrated circuit 100 of the system 200 against the tissue to be analysed;
2) substantially simultaneously illuminating the tissue with different light sources (a different light source for RAMAN and OCT and/or IR spectroscopy) e.g. at one or different locations of the tissue;
3) substantially simultaneously detecting scattered and reflected light, e.g. from one or different locations of the tissue, with the integrated circuit;
4) processing/correlating the detected scattered and reflected light;
5) calculating the concentration of the analyte using the processed/correlated data With substantially simultaneously it is meant that the illuminating and/or detecting is performed in such a time frame that the concentration in the tissue has not substantially varied.

The first light source is configured to emit a laser beam towards the tissue underneath the integrated circuit. The first light source may be a laser source suitable for continuous wave (CW) Raman spectroscopy, e.g. a high power laser diode with a wavelength of 785 nm. The first light source is optically coupled to the integrated circuit. The second light source is configured to emit a broadband light beam towards the tissue underneath the integrated circuit.

When RAMAN and OCT spectroscopic data is used to determine the concentration of an analyte in tissue, the second light source is configured for performing OCT spectroscopy. Integration of individual types of spectrometers such as RAMAN spectrometers, OCT spectrometers or IR spectrometers are known in the state of the art. An example of an OCT integrated spectrometer is for example given by systems available from Tornado spectral systems. The second light source may be a low coherent light source. The low coherence light source may be a LED, e.g. a super bright LED. For skin tissue applications, the wavelength of the low coherence light source is preferably in the optical transmission window between 700-900 nm. Alternatively, NIR (1000-1300 nm) wavelengths may also be used. The coherence length may be on the order of the substructures targeted for visualization, for example 10 to 100 um. The bandwidth depends on the exact specifications, but may be on the order of 10 to 100 nm.

When RAMAN and IR spectroscopic data is used to determine the concentration of an analyte in tissue, the second light source is configured for performing IR spectroscopy. The second light source may be a very wide bandwidth source. The second light source may be an LED, e.g. a super bright LED. The bandwidth may be 1.5 to 2.4 um. Alternatively, if the second light source is configured for performing IR spectroscopy, the second light source may be a thermal source.

According to an embodiment of the present invention, the optical coupling of the first and/or the second light source to the integrated circuit may be done by using an optical reflector. The optical reflector may be located on top of the integrated circuit (e.g. on top of a through-hole in the integrated circuit) or at an edge of the integrated circuit (e.g. on a support on which the integrated circuit is attached) thereby allowing the first and/or the second light source to illuminate the tissue underneath the integrated circuit. The use of an optical reflector is advantageous as the first and/or the second light source may be positioned parallel to the substrate thereby increasing compactness of the system. FIG. 5 illustrates an integrated circuit 100 with a through-hole 109. The optical reflector 205 is positioned on top of the through-hole 109, allowing a light beam to pass through the substrate 101 of the integrated circuit using a light source positioned parallel to the substrate 101.

According to an embodiment of the disclosure, the first light source may be optically coupled to the optical input of an optical waveguide distributor on the integrated circuit 100. Hence, a light beam of a laser may be distributed on the integrated circuit. As an advantage, different locations of the tissue underneath the integrated circuit 100 can be illuminated simultaneously. According to an embodiment of the disclosure, the second light source may be optically coupled to the optical input of an optical waveguide distributor for optically distributing a light beam of the second light source on the integrated circuit 100.

According to an embodiment of the disclosure, the read-out electronics may be electrically connected to the imaging region of the integrated circuit 100. The read-out electronics is used to read-out data from the imaging region. According to another embodiment of the disclosure, the read-out electronics may be electrically connected to the imaging region and the infrared imaging region of the integrated circuit 100. The read-out electronics may be used to read-out data from both imaging regions. The read-out electronics may comprise a central processing unit for processing data. The read-out electronics may further comprise a telecommunications module for transmitting data to other devices for external displaying or processing purposes. The telecommunication module may be a wireless communication module, e.g. a Wi-Fi, a Bluetooth or a ZigBee chip.

The integrated circuit, the first and second light source and the read-out electronics may be attached to a support. Alternatively, the integrated circuit, the first and second light source may be attached to a first support and the read-out electronics may be attached to a second support. The first support may be electrically connected to the second support via an electrical cable, e.g. a flexible electrical cable, thereby electrically interconnecting electrical components (e.g. image sensors to the read-out electronics) on both supports.

Figure 8:
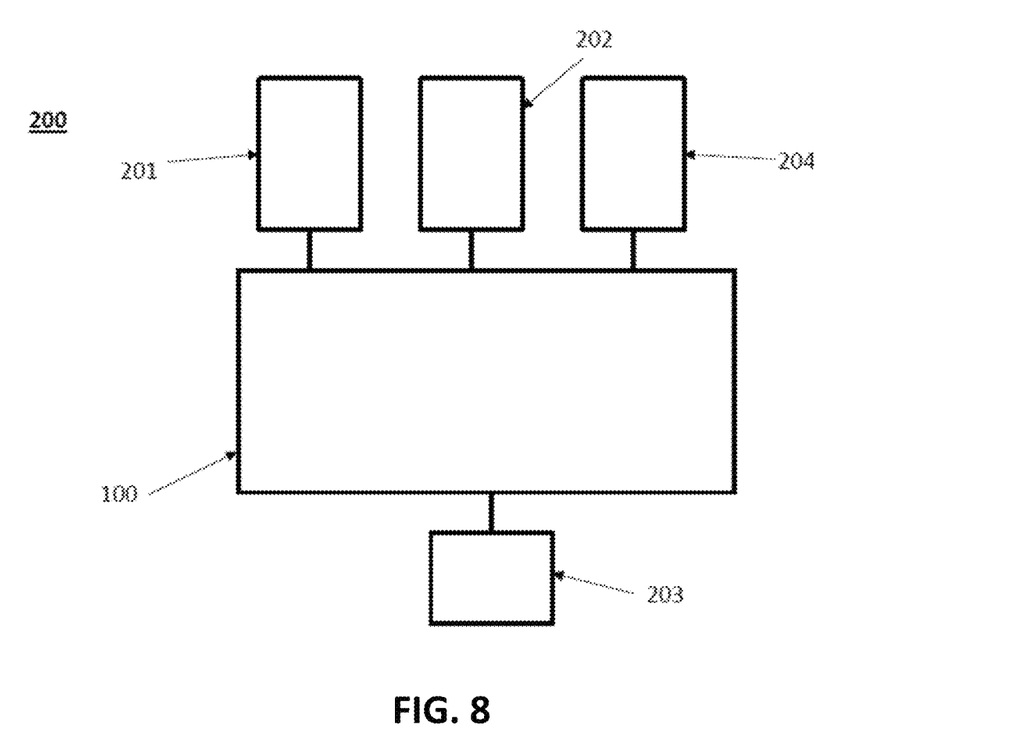
FIG. 8 illustrates a block diagram of a sensing system comprising an integrated circuit for performing RAMAN+OCT+IR spectroscopy according to an embodiment of the present invention.

According to an embodiment of the disclosure, the system 200 further comprises a third light source (204) optically coupled to the integrated circuit (100) and configured to emit a broadband light beam for performing IR spectroscopy or OCT spectroscopy; and wherein the read-out electronics (203) is further configured to read out and correlate spectroscopic data from the RAMAN, OCT and IR spectrometer and determine the concentration of an analyte using the correlated spectroscopic data.

The system 200 may be used to determine the concentration of an analyte in tissue in a non-invasive manner by combing RAMAN spectroscopy, OCT spectroscopy and IR spectroscopy. The system uses a third light source configured for performing IR spectroscopy or OCT spectroscopy. When the second light source is configured for performing IR spectroscopy, the third light source is configured for performing OCT spectroscopy. When the second light source is configured for performing OCT spectroscopy, the third light source is configured for performing IR spectroscopy. This configuration is illustrated in FIG. 8.

If the third light source if configured for performing OCT, the third light source is a low coherence light source. The low coherence light source may be a LED, e.g. a super bright LED. For skin tissue applications, the wavelength of the low coherence light source is preferably in the optical transmission window between 700-900 nm. Alternatively, NIR (1000-1300 nm) wavelengths may also be used. The coherence length may be on the order of the substructures targeted for visualization, for example 10 to 100 um. The bandwidth may be on the order of 10 to 100 nm.

If the third light source is configured for performing IR, the third light source is a very wide bandwidth source. The third light source may be a LED, e.g. a super bright LED. The bandwidth may be 1.5 to 2.4 um. Alternatively, if the third light source is configured for performing IR spectroscopy, the second light source may be a thermal source.

The optical coupling of the third light source to the integrated circuit may be done by using an optical reflector. The optical reflector may be located on top of the substrate (e.g. on top of a through-hole in the substrate) or at an edge of the substrate (e.g. on a support besides the substrate) thereby allowing the third light source to illuminate the tissue underneath the integrated circuit. The use of an optical reflector may be advantageous as the third light source may be positioned parallel to the substrate thereby increasing compactness of the system. The third light source may also be optically coupled to the optical input of an optical waveguide distributor on the integrated circuit.

The integrated circuit, the first, second and third light source and the read-out electronics may be attached to a support. Alternatively, the integrated circuit, the first, second and third light source may be attached to a first support and the read-out electronics may be attached to a second support. The first support may be electrically connected to the second support via an electrical cable, e.g. a flexible electrical cable, thereby electrically interconnecting electrical components on both supports.

According to an embodiment of the disclosure, the system further comprises a display unit electrically connected to the read-out electronics for displaying data processed by the read-out electronics, e.g. displaying the concentration of an analyte in the blood stream of an individual. The display unit may be an LCD or an OLED display.

According to an embodiment of the disclosure, the system 200 is completely packaged in a wearable casing wherein the wearable casing is adapted to press the integrated circuit 100 against skin tissue of an individual when worn thereby allowing illumination of the skin underneath the integrated circuit 100 and allowing reflected light from illuminated skin tissue to be received by the integrated circuit 100.

The system may be integrated in packaging allowing the integrated circuit to be in close contact with a tissue, e.g. skin tissue. The packaging may be adapted to press the integrated circuit as close as possible to the tissue, thereby allowing illumination of the tissue underneath the integrated circuit and maximizing detection of scattered and reflected light by the integrated circuit. The packaging may be a flexible packaging fabricated from an elastic material, e.g. a rubber. The system may be integrated in the packaging whereby a display unit of the system is visible to a user. When the integrated circuit comprises an optical window, the system may be integrated in the packaging whereby the optical window can directly contact the tissue.

According to an embodiment of the disclosure, the wearable casing is a wristband, the size of the wristband being adaptable to allow pressing of the integrated circuit 100 against the skin of an individual when worn. The wristband may be smart wristband in which the complete system 200 is integrated and allowing a close contact of the integrated circuit of the system with skin tissue of an individual when worn.

According to an embodiment of the disclosure, the wearable casing is a watch comprising a watch strap, the size of the watch strap being adaptable to allow pressing of the integrated circuit 100 against the skin of an individual when worn. The system may be part of a smart watch in which the complete system 200 is integrated and wherein the size of the watch strap can be adjusted thereby achieving a close contact of the integrated circuit with the skin of an individual when worn.

Figure 9:
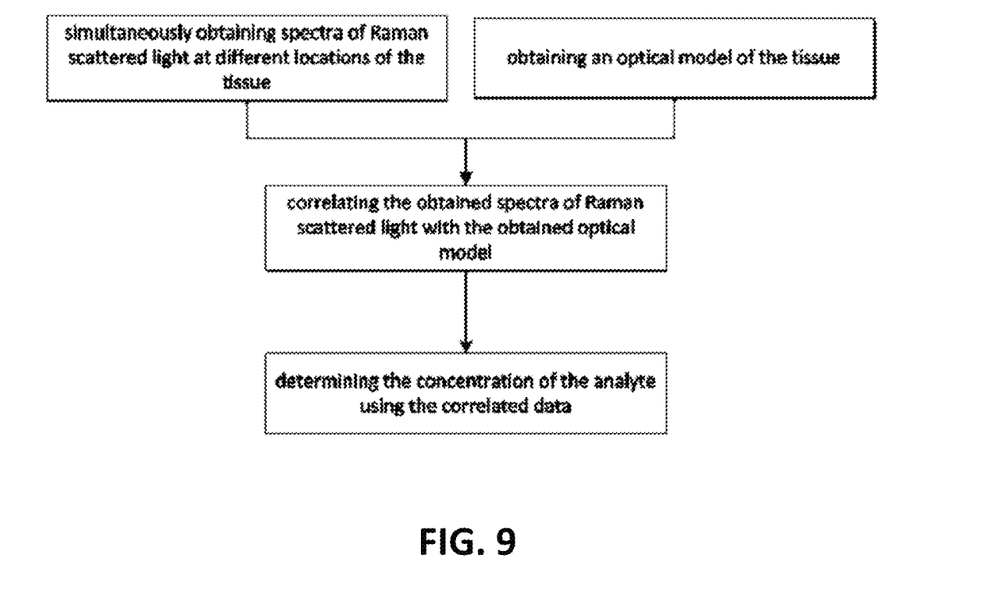
FIG. 9 illustrates a flow chart of a method to determine the concentration of an analyte in tissue according to an embodiment of the present invention.

In a fourth aspect of the disclosure, a method for non-invasive measuring of the concentration of an analyte in tissue using a sensor is presented. The method comprises: simultaneously obtaining spectra of Raman scattered light at one or different locations of the tissue underneath the sensor by illuminating the tissue underneath the sensor with a laser; receiving Raman scattered light, e.g. from one or from the different locations, of the tissue and extracting spectrum information from the Raman scattered light from the tissue; obtaining an optical model of the tissue underneath the sensor by illuminating the tissue underneath the sensor with a broadband light source, receiving reflected light and using spectral information of the received reflected light to extract optical properties of the tissue underneath the sensor; correlating the obtained spectra of Raman scattered light with the obtained optical model (the result of this step being a correlated data set); and determining the concentration of the analyte using the correlated data. Obtaining an optical model of the skin tissue is based on one or both of obtained OCT spectroscopic data and/or IR spectroscopic data. An exemplary flow chart is illustrated in FIG. 9.

The method allows determining the concentration of an analyte in tissue in a non-invasive way. An important aspect of some embodiments of the present invention is the simultaneous obtaining of spectra of Raman scattered light at different locations of the tissue. As muscle activity or blood vessel activity changes the volume of the tissue underneath the sensor, the spread of light inside the tissue changes over time. This has an impact on the spectra of Raman scattered light over time. Therefore, spectra of Raman scattered light advantageously are collected in a single snapshot. By doing so, it is also clear what the exact volume of the tissue underneath the sensor is.

The method can be performed using a sensor placed on top of tissue. The sensor may be pressed against the tissue and positioned to enable illumination of the tissue underneath the sensor. In some embodiments, a laser source may be used to simultaneously illuminate the tissue at different locations. Raman scattered light from one or different locations of the tissue is detected by the sensor. The spectrum of the Raman scattered light at each location of the tissue may be determined by spectrally resolving the Raman scattered light. Further, the tissue may be illuminated with a broadband light source and reflected light from the tissue may be detected by the sensor. From the detected reflected light, an optical model of the tissue underneath the sensor can be determined by extracting optical properties from the tissue underneath the sensor. The optical properties may be extracted from spectral information of the detected reflected light. The spectral information comprises amplitude and phase of the detected reflected light. The spectra of the Raman scattered light may be correlated with the optical model of the tissue underneath the sensor. Finally, the concentration of the analyte in the tissue may be determined using the correlated data.

Correlating the spectra of the Raman scattered light with the optical model of the tissue underneath the sensor may comprise correcting the Raman signals from different locations of the tissue using the optical model which comprises information on the volume and the type of skin tissue underneath the sensor. According to an embodiment of the disclosure, obtaining an optical model of the tissue comprises determining thickness and optical properties of different layers of the tissue. According to an embodiment of the disclosure, the tissue is skin tissue and determining an optical model of the tissue comprises determining a skin model of skin tissue underneath the sensor. The skin model comprises information on thickness and optical properties of different layers of the skin tissue.

According to an embodiment of the disclosure, the broadband light source comprises a low coherent light source and/or a very wide bandwidth source.

Determining a skin model may be performed by determining a number of parameters of a predetermined initial skin model using OCT and/or IR spectroscopic data. Such an initial skin model may comprise a number of layers representing different types of tissue, interstitial fluids, etc. With OCT and/or IR spectroscopic data, typical parameters of such layers such as thickness or refractive index or other optical properties can be determined for obtaining a model for the specific skin tissue measured.

When using a low coherent light source, the optical model may be determined by interfering the reflected light with a reference beam to call out phase information, resulting in an interferogram. The interferogram is used to determine the layer structure of tissue, e.g. skin tissue. This results in a measurement of the local geometry of the tissue, e.g. skin tissue. This technique is known as OCT spectroscopy. The low coherence light source may be a LED. For skin tissue applications, the wavelength of the low coherence light source is preferably in the optical transmission window between 700-900 nm. Alternatively, to increase penetration of the light beam in the tissue, near infrared NIR wavelengths from 1000-1300 nm may also be used. The coherence length may be on the order of the substructures targeted for visualization, for example 10 to 100 um. The bandwidth depends on the exact specifications and may be in the order of 10 to 100 nm.

When using a very wide bandwidth source, the reflected spectrum (diffuse reflectance, not specular) yields information about the types of molecules and, as a result, information on the type of tissue that is present in the tissue, e.g. in skin tissue. This additional information can be used to assess the local geometry of the tissue underneath the sensor. This technique is known as IR spectroscopy. The bandwidth of the very wide bandwidth source may be 1.5 to 2.4 um. As an advantage, when using IR spectroscopy, the skin model further comprises information on the refractive index of interstitial fluid and blood in skin tissue. The information on the refractive index of interstitial fluid and blood in the skin tissue correlates with glucose concentration in the blood. As an advantage, the method can be used to accurately measure glucose concentration in the human body in a non-invasive manner.

According to an embodiment of the disclosure, obtaining spectra of Raman scattered light from one or different locations of the tissue and obtaining an optical model of the tissue is performed simultaneously. As an advantage, the method may be performed faster. As a further advantage, as both steps may be performed at the same time, the volume of the tissue being probed is the same for both techniques. This results in a correct determination of the concentration of an analyte in the tissue.

When performing Raman and OCT spectroscopy simultaneously, the wavelength of reflected light for performing OCT and the wavelength of Raman scattered light may be separated to prevent interference. According to an embodiment of the disclosure, determining an optical model of the tissue is done using OCT and IR spectroscopy. Performing OCT and IR spectroscopy may be performed substantially simultaneously. The combination delivers a more accurate optical model of the tissue thereby resulting in a more accurate determination of the concentration of an analyte in the tissue. Further, RAMAN, IR and OCT spectroscopy may be performed simultaneously. As a result, the same volume of the tissue underneath the sensor is probed, resulting in increased accuracy of the correlated data of the three spectroscopy techniques.

Figure 10:
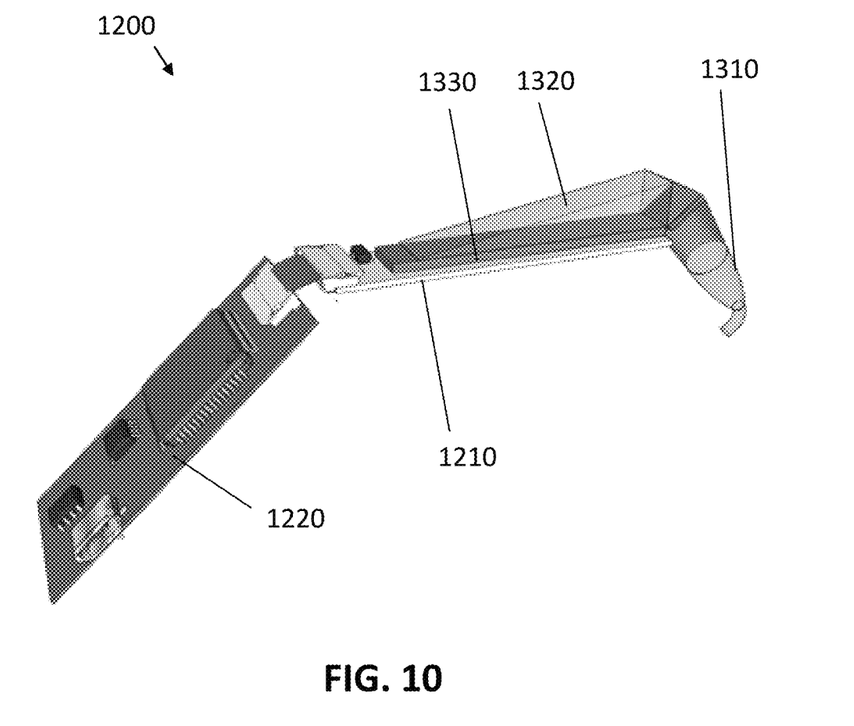
FIG. 10 provides a schematic 3D drawing of a detector system in accordance with embodiments of the present invention.
Figure 11:
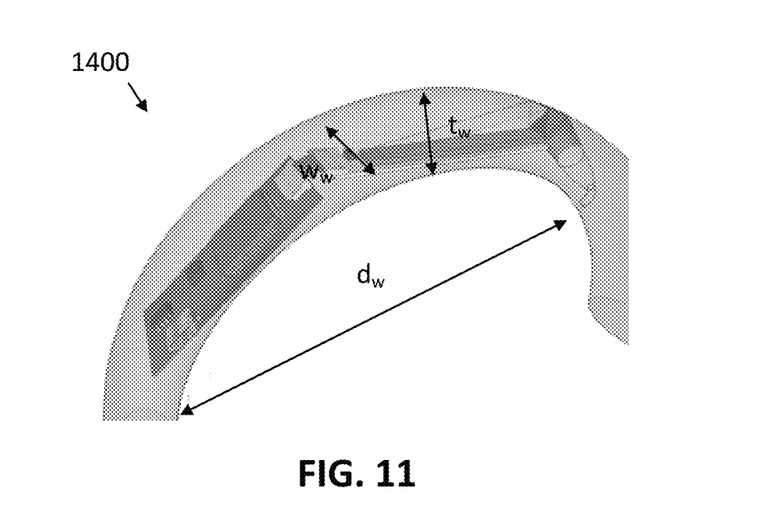
FIG. 11 provides a schematic 3D drawing of a detector system comprising a wrist band in accordance with embodiments of the present invention.

By way of illustration, embodiments of the present invention not being limited thereto, an example of a system and a system embedded in a wristband is shown in FIG. 10 and FIG. 11. FIG. 10 illustrates a detector system 1200. The detector system 1200 comprises an optical system as described above being part of an optical printed circuit board 1210, including the optical part of the spectrometer. The optical system shows a collimator 1310, a beam shaping and coupling element 1320 and a spectrometer chip 1330. The detector system 1200 moreover comprises a read-out printed circuit board 1220 for reading out the optical signal received from the optical part of the spectrometer. The read-out printed circuit board 1220 is connected with the optical printed circuit board 1210. The read-out printed circuit board 1220 digitizes the optical signal coming from the optical system and/or processes the digitized result. An exemplary embodiment thereof is shown in FIG. 10.

An example of an embodiment wherein the optical system and the read-out printed circuit board 1220 are integrated in a wristband 1400 is shown in FIG. 11. In the exemplary embodiment illustrated in FIG. 11 the dimensions $d_w$, $t_w$, and $w_w$ are indicated. An example of a set of possible dimensions may be as follows: $d_w$=6.5 cm, $t_w$=7.4 mm, and $w_w$=14 mm. Due to the small thickness of the optical system, the wristband can be limited in height, resulting in a high degree of wearability.

The invention claimed is:

1. A wearable system for non-invasive measuring of a concentration of an analyte in skin tissue, the wearable system comprising:
    a first light source configured to emit a laser beam that facilitates performance of Raman spectroscopy;
    a second light source configured to emit a broadband light beam that facilitates performance of optical coherence tomography (OCT) spectroscopy and infrared (IR) spectroscopy;
    at least one optical waveguide distributor optically coupled to one of the first light source or the second light source, wherein the at least one optical waveguide distributor comprises a plurality of optical outputs through which light from the first light source or the second light source is simultaneously distributed to multiple discrete locations of the skin tissue;
    an integrated circuit comprising a first substrate, a second substrate on the first substrate, and a third substrate on the second substrate, wherein each substrate comprises an optical unit that defines a through-hole through which light passes, wherein the through-holes of the optical units are aligned with one another to define a through-hole in the integrated circuit through which reflected light from a particular location of the skin tissue passes, wherein each optical unit comprises:
        a light coupler that wraps around the through-hole of the optical unit and that is configured to optically communicate scattered or reflected light from illuminated skin tissue that falls within a wavelength range, wherein a particular wavelength range for each light coupler is different for each substrate;
        a Raman spectrometer optically coupled to the light coupler;
        an OCT spectrometer optically coupled to the light coupler;
        an IR spectrometer optically coupled to the light coupler;
        an interferometer optically coupled to the OCT spectrometer; and
        one or more imaging regions optically coupled to the Raman spectrometer, the OCT spectrometer, and the IR spectrometer, wherein the one or more imaging regions are configured to convert optical signals communicated from the Raman spectrometer, the OCT spectrometer, and the IR spectrometer to data; and circuitry coupled to the one or more imaging regions of each substrate, wherein the circuitry is configured to determine the concentration of the analyte based on the data.

2. The wearable system according to claim 1, wherein the wearable system is integrated in flexible packaging allowing the integrated circuit to be in contact with skin tissue, and wherein the flexible packaging is fabricated from an elastic material.

3. The wearable system according to claim 1, wherein the circuitry is further configured to determine a refractive index of interstitial fluid and blood in the skin tissue, and wherein the circuitry is configured to read out spectroscopic data from the Raman spectrometers simultaneously with spectroscopic data from the OCT spectrometers or the IR spectrometers.

4. The wearable system according to claim 1, wherein the light coupler of a first optical unit is configured to couple light within a first wavelength range into the Raman spectrometer of the first optical unit, wherein the light coupler of a second optical unit is configured to couple light within a second wavelength range into the Raman spectrometer of the second optical unit, wherein the light coupler of a third optical unit is configured to couple light within a third wavelength range into the Raman spectrometer of the third optical unit, wherein the first wavelength range is adjacent to the second wavelength range, and wherein the second wavelength range is adjacent to the third wavelength range.

5. The wearable system according to claim 1, further comprising:
  a first isolating layer positioned between the first substrate and the second substrate; and
  a second isolating layer positioned between the second substrate and the third substrate.

6. The wearable system according to claim 1, wherein the wearable system is packaged in a wearable casing, wherein the wearable casing is adapted to press the integrated circuit against the skin tissue of an individual when worn, thereby allowing scattered and reflected light from illuminated skin tissue to be received by the integrated circuit, wherein the wearable casing is a wristband, and wherein a size of the wristband is configured to facilitate pressing of the integrated circuit against the skin tissue of the individual when worn.

7. The wearable system according to claim 1, wherein the wearable system is packaged in a wearable casing, wherein the wearable casing is configured to press the integrated circuit against the skin tissue of an individual when worn, thereby allowing scattered and reflected light from illuminated skin tissue to be received by the integrated circuit, wherein the wearable casing is a watch comprising a watch strap, and wherein a size of the watch strap is configured to facilitate pressing of the integrated circuit against the skin tissue of the individual when worn.

8. The wearable system according to claim 1, further comprising a third light source optically coupled to the integrated circuit and configured to emit a broadband light beam, wherein the second light source and the third light source each provide a broadband light beam to one or more of the IR spectrometers or one or more of the OCT spectrometers, and wherein the circuitry is further configured to correlate spectroscopic data from the Raman spectrometers, OCT spectrometers, and IR spectrometers and determine the concentration of the analyte based on the correlated spectroscopic data.

9. The wearable system according to claim 8, wherein the second light source is a low-coherence light source or a wide bandwidth source, and wherein the third light source is a low-coherence light source or a wide bandwidth source.

10. The wearable system according to claim 1, further comprising at least one optical reflector adapted to couple light from the integrated circuit.

11. A method for non-invasive measuring of a concentration of an analyte in skin tissue, the method comprising:
  simultaneously obtaining spectra of Raman scattered light and one or both of optical coherence tomography (OCT) spectra and infrared (IR) spectra in a non-invasive way from multiple discrete locations of the skin tissue via a wearable system, wherein the wearable system comprises:
    a first light source configured to emit a laser beam that facilitates performance of Raman spectroscopy;
    a second light source configured to emit a broadband light beam that facilitates performance of optical coherence tomography (OCT) spectroscopy and infrared (IR) spectroscopy;
    at least one optical waveguide distributor optically coupled to one of the first light source or the second light source, wherein the at least one optical waveguide distributor comprises a plurality of optical outputs through which light from the first light source and the second light source is simultaneously distributed to multiple discrete locations of the skin tissue;
    an integrated circuit comprising a first substrate, a second substrate on the first substrate, and a third substrate on the second substrate, wherein each substrate comprises an optical unit that defines a through-hole through which light passes, wherein the through-holes of the optical units are aligned with one another to define a through-hole in the integrated circuit through which reflected light from a particular location of the skin tissue passes, wherein each optical unit comprises:
      a light coupler that wraps around the through-hole of the optical unit and that is configured to optically communicate scattered or reflected light from illuminated skin tissue that falls within a wavelength range, wherein a particular wavelength range for each light coupler is different for each substrate;
      a Raman spectrometer optically coupled to the light coupler;
      an OCT spectrometer optically coupled to the light coupler;
      an IR spectrometer optically coupled to the light coupler;
      an interferometer optically coupled to the OCT spectrometer; and
      one or more imaging regions optically coupled to the Raman spectrometer, the OCT spectrometer, and the IR spectrometer, wherein the one or more imaging regions are configured to convert optical signals communicated from the Raman spectrometer, the OCT spectrometer, and the IR spectrometer to data; and
  correlating, by circuitry coupled to the one or more imaging regions of each substrate, the obtained spectra of Raman scattered light with the obtained OCT spectra or IR spectra; and
  determining, by the circuitry, the concentration of the analyte using the correlation between the obtained spectra of Raman with the obtained OCT spectra or IR spectra.

12. The method according to claim 11, wherein the wearable system is integrated in flexible packaging allowing the integrated circuit to be in contact with skin tissue, and wherein the flexible packaging is fabricated from an elastic material.

13. The method according to claim 11, further comprising determining, by the circuitry, a refractive index of interstitial fluid and blood in the skin tissue.

14. The method according to claim 11, wherein simultaneously obtaining spectra of Raman scattered light and one or both of OCT spectra and IR spectra comprises simultaneously obtaining spectra of Raman scattered light, OCT spectra, and IR spectra.

15. The method according to claim 11, wherein the skin tissue is disposed underneath the wearable system.

16. The method according to claim 11, wherein the integrated circuit is a complimentary metal-oxide-semiconductor (CMOS) chip.

17. The method according to claim 11, wherein the analyte is glucose.

18. The method according to claim 11, further comprising determining, by the circuitry, thicknesses and optical properties of different layers of the skin tissue.

19. A central processing unit for processing data configured to execute a method for non-invasive measuring of a concentration of an analyte in skin tissue, the method comprising:
   simultaneously obtaining spectra of Raman scattered light and one or both of optical coherence tomography (OCT) spectra and infrared (IR) spectra in a non-invasive way from multiple discrete locations of the skin tissue via a wearable system, wherein the wearable system comprises:
      a first light source configured to emit a laser beam that facilitates performance of Raman spectroscopy;
      a second light source configured to emit a broadband light beam that facilitates performance of optical coherence tomography (OCT) spectroscopy and infrared (IR) spectroscopy;
      at least one optical waveguide distributor optically coupled to one of the first light source or the second light source, wherein the at least one optical waveguide distributor comprises a plurality of optical outputs through which light from the first light source and the second light source is simultaneously distributed to multiple discrete locations of the skin tissue;
   an integrated circuit comprising a first substrate, a second substrate on the first substrate, and a third substrate on the second substrate, wherein each substrate comprises an optical unit that defines a through-hole through which light passes, wherein the through-holes of the optical units are aligned with one another to define a through-hole in the integrated circuit through which reflected light from a particular location of the skin tissue passes, wherein each optical unit comprises:
   a light coupler that wraps around the through-hole of the optical unit and that is configured to optically communicate scattered or reflected light from illuminated skin tissue that falls within a wavelength range, wherein a particular wavelength range for each light coupler is different for each substrate;
   a Raman spectrometer optically coupled to the light coupler;
   an OCT spectrometer optically coupled to the light coupler;
   an IR spectrometer optically coupled to the light coupler;
   an interferometer optically coupled to the OCT spectrometer; and
   one or more imaging regions optically coupled to the Raman spectrometer, the OCT spectrometer, and the IR spectrometer, wherein the one or more imaging regions are configured to convert optical signals communicated from the Raman spectrometer, the OCT spectrometer, and the IR spectrometer to data; and
   correlating, by circuitry coupled to the one or more imaging regions of each substrate, the obtained spectra of Raman scattered light with the obtained OCT spectra or IR spectra;
   determining, by the circuitry, thicknesses and optical properties of different layers of the skin tissue and the concentration of the analyte using the correlation between the obtained spectra of Raman with the obtained OCT spectra or IR spectra.

* * * * *